(12) United States Patent
Lee et al.

(10) Patent No.: US 9,024,084 B2
(45) Date of Patent: May 5, 2015

(54) REDUCED ENERGY ALCOHOL SEPARATION PROCESS HAVING CONTROLLED PRESSURE

(75) Inventors: David Lee, Seabrook, TX (US); Adam Orosco, Houston, TX (US); R. Jay Warner, Houston, TX (US); Victor J. Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 582 days.

(21) Appl. No.: 13/456,548

(22) Filed: Apr. 26, 2012

(65) Prior Publication Data

US 2012/0277492 A1 Nov. 1, 2012

Related U.S. Application Data

(63) Continuation-in-part of application No. 13/094,588, filed on Apr. 26, 2011, now Pat. No. 8,686,200, and a continuation-in-part of application No. 13/292,914, filed on Nov. 9, 2011, now Pat. No. 8,927,784.

(60) Provisional application No. 61/590,009, filed on Jan. 24, 2012.

(51) Int. Cl.
| | |
|---|---|
| *C07C 29/149* | (2006.01) |
| *C07C 51/12* | (2006.01) |
| *C07C 29/80* | (2006.01) |
| *C07C 67/08* | (2006.01) |
| *C07C 67/54* | (2006.01) |

(52) U.S. Cl.
CPC ............... *C07C 51/12* (2013.01); *C07C 29/149* (2013.01); *C07C 29/80* (2013.01); *C07C 67/08* (2013.01); *C07C 67/54* (2013.01)

(58) Field of Classification Search
CPC .................................................... C07C 29/149
USPC ......................................... 568/885, 913, 918
See application file for complete search history.

(56) References Cited

U.S. PATENT DOCUMENTS

| | | | |
|---|---|---|---|
| 2,607,807 A | 8/1952 | Ford | |
| 2,649,407 A | 8/1953 | Harrison et al. | |
| 2,702,783 A | 2/1955 | Harrison et al. | |
| 2,801,209 A | 7/1957 | Muller et al. | |
| 2,882,244 A | 4/1959 | Milton | |
| 3,102,150 A | 8/1963 | Hunter et al. | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,769,329 A | 10/1973 | Knox et al. | |
| 3,990,952 A | 11/1976 | Katzen et al. | |
| 4,126,539 A | 11/1978 | Derr, Jr. et al. | |
| 4,149,940 A | 4/1979 | Pinto | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulpranthipanja et al. | |
| 4,352,940 A | 10/1982 | Adelman et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,443,639 A | 4/1984 | Pesa et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,842,693 A | 6/1989 | Wheldon | |
| 4,886,905 A | 12/1989 | Larkins et al. | |
| 4,908,477 A | 3/1990 | Hartmann et al. | |
| 4,961,826 A | 10/1990 | Grethlein et al. | |

(Continued)

FOREIGN PATENT DOCUMENTS

| | | |
|---|---|---|
| CN | 201768393 | 3/2011 |
| CN | 102228831 | 11/2011 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

J. Jones, et al., Platinum Metals Review, vol. 44, No. 3, pp. 94-104 (Jul. 2000).

(Continued)

*Primary Examiner* — Elvis O Price

(57) ABSTRACT

The present invention is directed to processes for the recovery of ethanol from a crude ethanol product obtained from the hydrogenation of acetic acid using a low energy process. The crude ethanol product is separated in one or more columns. At least one of the columns is operated at a controlled pressure to enhance separation of ethanol and organics. In one embodiment, there are at least two columns that operate at controlled pressures.

31 Claims, 2 Drawing Sheets

(56) References Cited

U.S. PATENT DOCUMENTS

| | | |
|---|---|---|
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2006/0019360 A1 | 1/2006 | Verser et al. |
| 2006/0127999 A1 | 6/2006 | Verser et al. |
| 2007/0031954 A1 | 2/2007 | Mairal et al. |
| 2007/0106246 A1 | 5/2007 | Modesitt |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |
| 2012/0273338 A1 | 11/2012 | Lee |
| 2012/0323049 A1 | 12/2012 | Lee |
| 2012/0323050 A1 | 12/2012 | Lee |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |

(56) References Cited

FOREIGN PATENT DOCUMENTS

| | | |
|---|---|---|
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 | 8/2011 |
| WO | WO 2011/097227 | 8/2011 |
| WO | WO 2011/140485 | 11/2011 |
| WO | WO 2012/006219 | 1/2012 |
| WO | WO 2012/006228 | 1/2012 |
| WO | WO 2012/006499 | 1/2012 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Witzeman and Agreda, "Safety and Performance Assessment of Ethanol/Diesel Blends (e-blend)" NREL/SR-540-34817, at p. 1-1, Sep. 2003.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 pages).

H. Constantin et al., "Influence of C-Sources on the Denitrification Rate of a High-Nitrate Concentrated Industrial Wastewater", Wat. Res. vol. 31, No. 3, 1997, pp. 583-589.

V. Ragaini et al., "Increasing the value of dilute acetic acid streams through esterification Part 1. Experimental analysis of the reaction zone", Applied Catalysis B: Environmental, vol. 64, 2006, pp. 66-71.

Anonymous: "Studies in Extractive and Azeotropic Distillation Series; Study No. 4—Separation of Alcohols from the Acetate/Alcohol/Water Ternary by Extractive Distillation" May 9, 2008, pp. 1-9.

Kita H., et al., "Synthesis of a Zeolite NAA Membrane for Pervaporation of Water/Organic Liquid Mixtures", Journal of Materials Science Letters, vol. 14, Jan. 1, 1995, pp. 206-208.

Calvar, et al., "Esterification of acetic acid and ethanol: Reaction kinetics and operation in a packed bed reactive distillation column", Chem Engineering and Processing, vol. 46, No. 12, Oct. 9, 2007, pp. 1317-1323.

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

Benson, Tracy J., et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701.

Yu Huang, et al., "Low-Energy Distillation-Membrane separation Process", Industrial & Engineering Chemistry Research, Am. Chem. Soc., vol. 49, No. 8, Jan. 1, 2010, pp. 3760-3768.

International Search Report and Written Opinion for PCT/US2011/023276 mailed Sep. 2, 2011.

International Search Report and Written Opinion for PCT/US2012/035273 mailed Jul. 30, 2012.

International Search Report and Written Opinion for PCT/US2012/035220 mailed Aug. 2, 2012.

International Search Report and Written Opinion for PCT/US2011/060014 mailed Jun. 29, 2012.

International Search Report and Written Opinion for PCT/US2011/060019 mailed Apr. 19, 2012.

International Search Report and Written Opinion for PCT/US2012/035189 mailed Jul. 30, 2012.

International Search Report and Written Opinion for PCT/US2012/035196 mailed Aug. 6, 2012.

International Search Report and Written Opinion for PCT/US2011/059889 mailed Jul. 6, 2012.

International Search Report and Written Opinion for PCT/US2012/035203 mailed Jul. 11, 2012.

Jakobsson, et al., "Modelling of a side reactor configuration combining reaction and distillation", Chemical Engineering Science, vol. 57, No. 9, May 1, 2002, pp. 1521-1524.

Xu, et al., "Kinetics of acetic acid esterification over ion exchange catalysts", Canadian Journal of Chemical Engineering, vol. 74, Aug. 1, 1996, pp. 493-500.

International Search Report and Written Opinion for PCT/US2012/035194 mailed Nov. 15, 2012.

International Search Report and Written Opinion for PCT/US2012/035198 mailed Oct. 30, 2012.

International Search Report and Written Opinion for PCT/US2012/035208 mailed Nov. 9, 2012.

International Search Report and Written Opinion for PCT/US2012/035271 mailed Nov. 12, 2012.

International Search Report and Written Opinion for PCT/US2012/035175 mailed Nov. 15, 2012.

Response to Final Office Action for U.S. Appl. No. 13/162,005, filed Nov. 26, 2013.

Response to Final Office Action for U.S. Appl. No. 13/162,034, filed Nov. 27, 2013.

International Preliminary Report on Patentability for PCT/US2012/035194 mailed Nov. 7, 2013.

REDUCED ENERGY ALCOHOL SEPARATION PROCESS HAVING CONTROLLED PRESSURE

CROSS REFERENCE TO RELATED APPLICATION

This application claims priority to U.S. App. No. 61/590,009, filed on Jan. 24, 2012, the entire contents and disclosures of which are incorporated herein by reference. This application is a continuation-in-part of U.S. application Ser. No. 13/094,588, filed on Apr. 26, 2011, and is also a continuation-in-part of U.S. application Ser. No. 13/292,914, filed on Nov. 9, 2011, the entire contents and disclosures of which are incorporated herein by reference.

FIELD OF THE INVENTION

The present invention relates generally to processes for producing alcohol and, in particular, to a process for recovering ethanol from an ethyl acetate residue stream using one or more columns, and operating the columns under a controlled pressure when recovering ethanol in the residue. In one preferred embodiment, there are at least two columns that operate under a controlled pressure.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acids, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selective and catalyst activity and operating life for the conversion of hydrocarbons to ethanol and optionally acetic acid in the presence of a particulate catalyst, said conversion proceeds via a syngas generation intermediate step.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and ethyl acetate and a first residue comprising ethanol, acetic acid, and water; separating a portion of the first residue in a second distillation column to yield a second residue comprising acetic acid and water and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated at a lower pressure than the second distillation column. In one embodiment, the first and third columns are operated at a pressure from 0.1 kPa to 102 kPa, and preferably below atmospheric pressure. In one embodiment, the second distillation column is operated above 70 kPa, e.g. 70 kPa to 510 kPa. The first and/or third columns may be operated at least 10 kPa lower than the second column.

In a second embodiment, the present invention is directed to a process for producing ethanol comprising providing a crude ethanol product comprising ethanol, acetic acid, ethyl acetate, acetaldehyde, and water; separating a portion of the crude ethanol product in a first distillation column to yield a first distillate comprising acetaldehyde and ethyl acetate and a first residue comprising ethanol, ethyl acetate, acetic acid, and water; separating a portion of the first residue in a second distillation column to yield a second residue comprising acetic acid and water and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated at a lower pressure than the second distillation column.

In a third embodiment, the present invention is directed to a process for producing ethanol comprising providing a crude ethanol product comprising ethanol, ethyl acetate, acetaldehyde, and water; separating at least a portion of the crude ethanol product in a first distillation column to form a first distillate comprising acetaldehyde and ethyl acetate and a first residue comprising ethanol and water; separating at least a portion of the first residue to form an organic stream comprising ethanol and an aqueous stream comprising water; and separating the organic stream in a second distillation column to form a second distillate comprising ethanol and a second residue comprising water, wherein the first distillation column is operated at a lower pressure than the second distillation column.

In a fourth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and ethyl acetate and a first residue comprising ethanol, ethyl acetate, acetic acid and water; separating a portion of the first residue in a second distillation column to yield a second residue comprising acetic acid and a second distillate comprising ethanol, ethyl acetate and water; removing water from at least a portion of the second distillate to yield an ethanol product having a lower water content than the at least a portion of the second distillate; and separating at least a portion of the ethanol product in a third distillation column to yield a third distillate comprising ethyl acetate and a third residue comprising ethanol and less than 3 wt. % water, wherein the first distillation column and the third distillation column are operated at a lower pressure than the second distillation column.

In a fifth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and ethyl acetate and a first residue comprising ethanol, acetic acid and water; separating a portion of the first residue in a second distillation column to yield a second residue comprising acetic acid and water and a second distillate comprising ethanol, and ethyl acetate; separating at least a portion of the second distillate in a third distillation column to yield a third distillate comprising ethyl acetate and a third residue comprising ethanol; and returning at least a portion of the third distillate to the first distillation column; wherein the first distillation column and third distillation column are operated at a lower pressure than the second distillation column.

In a sixth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and a first residue comprising ethanol, acetic acid and/or ethyl acetate; separating a portion of the first residue in a second distillation column to yield a second residue comprising high boiling point components and a second distillate comprising ethanol and ethyl acetate; and separating at least a portion of the second distillate in a third distillation column to yield a third distillate comprising ethyl acetate and a third residue comprising ethanol, wherein the first distillation column and/or third distillation column are operated at a lower pressure than the second distillation column.

In a seventh embodiment, the present invention is directed to a process for producing ethanol comprising: hydrogenating acetic acid and/or an ester thereof in a reactor in the presence of a catalyst to form a crude ethanol product; separating a portion of the crude ethanol product in a first distillation column to yield a first distillate comprising acetaldehyde and a first residue comprising ethanol, acetic acid and/or ethyl acetate; separating a portion of the first residue in a second distillation column to yield a second residue comprising high boiling point components and a second distillate comprising ethanol and ethyl acetate; and separating at least a portion of the second distillate in a third distillation column to yield a third distillate comprising ethyl acetate and a third residue comprising ethanol, wherein the first distillation column and third distillation column are operated below atmospheric pressure.

In an eighth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column that is an extractive column with an extractive agent comprising water to yield a first distillate comprising acetaldehyde and ethyl acetate and a first residue comprising ethanol, acetic acid, and water; separating a portion of the first residue in a second distillation column to yield a second residue comprising acetic acid and water and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated at a lower pressure than the second distillation column.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1:
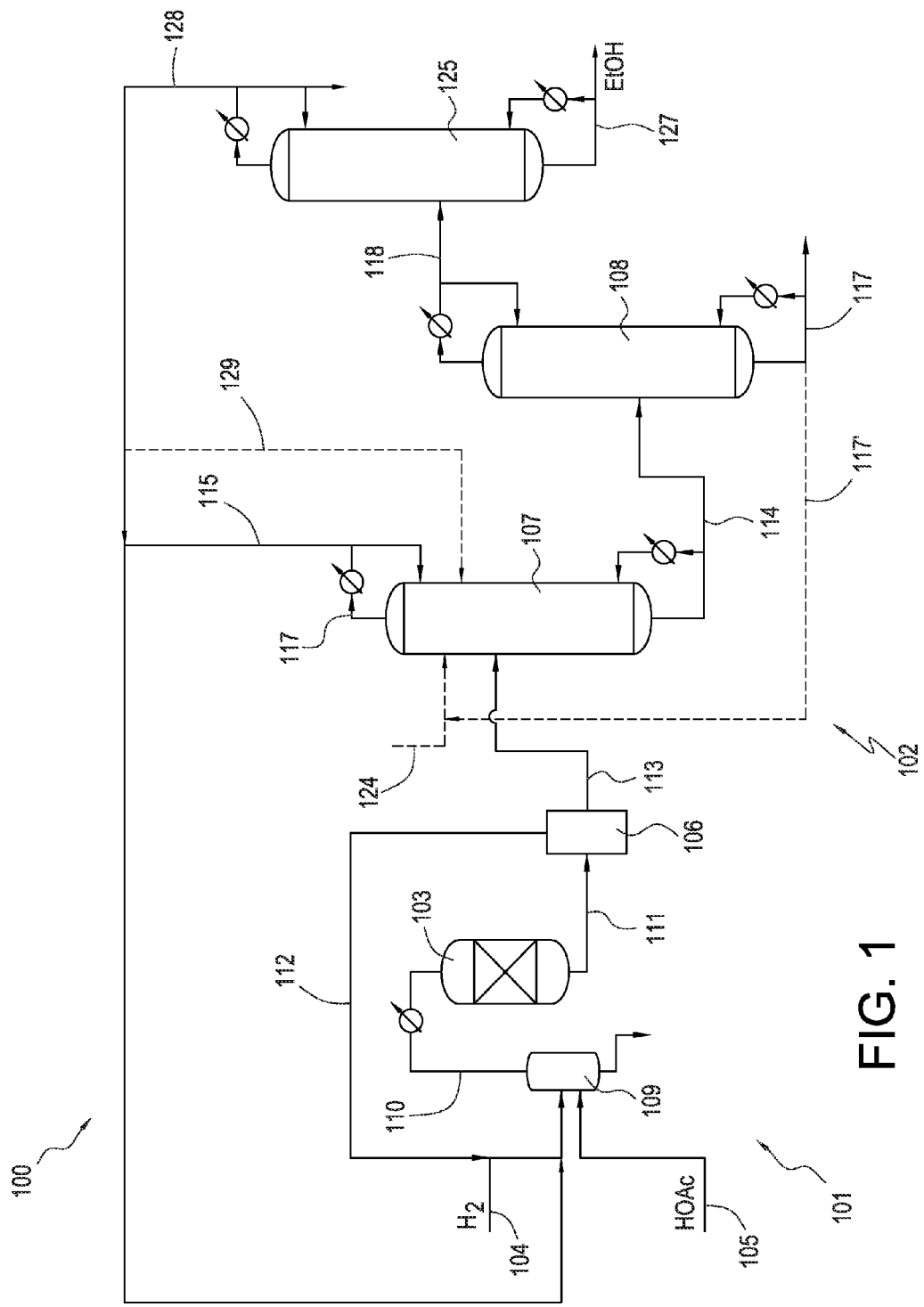
FIG. 1 is a schematic diagram of an ethanol production system with multiple distillation columns to recover ethanol including an acid column in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, acetaldehyde, acetic acid, and other impurities. Water is co-produced with ethanol in the hydrogenation reaction in about a 1:1 molar ratio, and thus producing ethanol also results in the production of water. This makes recovering industrial grade ethanol or fuel grade ethanol difficult due to the excess water. The processes of the present invention involve separating the crude ethanol product through one or more separation columns such that the columns are operated under a controlled pressure. In one preferred embodiment, there are three columns and the first and third columns are operated at a controlled pressure that is lower pressure than the second column. When the first and third columns are operated under a controlled pressure, the energy requirements for the overall process may be decreased. Without being bound by theory, it is believed that the volatility of ethanol, ethyl acetate and other organic compounds in the crude ethanol product increases as pressure decreases. Increased volatility may lead to improved separation efficiencies and ultimately to an increase in ethanol production. Thus, improved separation efficiencies may lower capital costs and at the same time increase ethanol production. The present invention uses two columns under a controlled pressure to obtain an ethanol product having reduced organic impurities.

In accordance with the present invention, the exemplary embodiments comprise of three columns, the first and third columns may be operated at the same or different controlled pressures. Generally, the pressure of the first and third columns may be below atmospheric pressure. The pressure of the second column may be the same as, less than or greater than the first and/or third column. In a preferred embodiment, the pressure of the second column is greater than the pressure of the first and/or third column. In some embodiments, the first and/or third columns may be operated at least 10 kPa lower than the second column, e.g., at least 30 kPa lower or at least 50 kPa lower. In one embodiment, the first and third columns are operated at a pressure from 0.1 kPa to 102 kPa, e.g., from 0.1 kPa to 70 kPa, from 1 kPa to 60 kPa, or from 1 kPa to 50 kPa. The second column may be operated at a pressure from 0.1 kPa to 510 kPa, e.g., from 70 kPa to 510 kPa, from 70 kPa to 475 kPa, from 70 kPa to 350 kPa or from 70 kPa to 200 kPa.

The crude ethanol product may be separated in a first column into a first residue stream comprising ethanol, water, ethyl acetate and acetic acid and a first distillate stream comprising acetaldehyde and ethyl acetate. The first column primarily removes light organics in the distillate and returns those organics for subsequent hydrogenation. The first column may be an extractive distillation column. In some embodiments, the extractive agent is water. The water may be added to the column as an extractive agent from an external source or from within the process as a recycle stream.

In a second column, the first residue stream is further separated to yield a second residue comprising acetic acid and water and a second distillate comprising ethanol and ethyl acetate. The second distillate may be further separated in a third column to yield a third distillate comprising ethyl acetate and a third residue comprising ethanol. Ethyl acetate may be removed in both the first and third columns. Subsequently, the ethanol is removed from the residue stream to yield an ethanol product. Advantageously, this separation approach results in reducing energy requirements to recover ethanol from the crude ethanol product.

By operating both the first and third columns at a controlled pressure that is preferably lower than the second column, separation efficiency may be improved while simultaneously reducing energy requirements. In other embodiments, the second column may also be operated below atmospheric pressure provided that the pressure of the second column is greater than the first and/or third column.

In preferred embodiments, the first residue stream comprises a substantial portion of the ethanol, water and acetic acid from the crude ethanol product. The first residue stream, for example, may comprise at least 50% of the ethanol from the crude ethanol product, and more preferably at least 70%. In terms of exemplary ranges, the first residue stream may comprise from 50% to 99.9% of the ethanol from the crude ethanol product, and more preferably from 70% to 99%. The amount of ethanol from the crude ethanol recovered in the residue may be greater than 97.5%, e.g. greater than 99.9%.

Depending on the ethyl acetate concentration in the residue and whether there is in situ esterification in the residue or an esterification reactor, it may be necessary to further separate the ethyl acetate and ethanol in a separate column. Preferably, this separate column is located after the water has been removed using a distillation column and water separator. Generally, a separate column may be necessary when the residue comprises at least 10 wppm or at least 50 wppm ethyl acetate or there is esterification. When the ethyl acetate is less than 50 wppm it may not be necessary to use separate column to separate ethyl acetate and ethanol.

In preferred embodiments, the residue stream comprises a substantial portion of the water and the acetic acid from the crude ethanol product. The residue stream may comprise at least 80% of the water from the crude ethanol product, and more preferably at least 90%. In terms of ranges, the residue stream preferably comprises from 80% to 100% of the water from the crude ethanol product, and more preferably from 90% to 99.4%. The residue stream may comprise at least 85% of the acetic acid from the crude ethanol product, e.g., at least 90% and more preferably about 100%. In terms of ranges, the residue stream preferably comprises from 85% to 100% of the acetic acid from the crude ethanol product, and more preferably from 90% to 100%. In one embodiment, substantially all of the acetic acid is recovered in the residue stream.

The residue stream comprising ethanol, ethyl acetate, water, and acetic acid may be further separated to recover ethanol. Because these compounds may not be in equilibrium, additional ethyl acetate may be produced through esterification of ethanol and acetic acid. In one preferred embodiment, the water and acetic acid may be removed as another residue stream in a separate distillation column. In addition, the water carried over in the separate distillation column may be removed with a water separator that is selected from the group consisting of an adsorption unit, membrane, extractive distillation column, molecular sieves, or a combination thereof.

In an exemplary embodiment, the total energy requirements in the separation process according to the present invention may be less than 5 MMBtu per ton of refined ethanol, e.g., less than 4.5 MMBtu per ton of refined ethanol or less than 4.25 MMBtu per ton of refined ethanol.

In one embodiment each of the columns is sized to be capital and economically feasible for the rate of ethanol production. The total diameter for the columns used to separate the crude ethanol product may be from 5 to 40 meters, e.g., from 10 to 30 meters or from 12 to 20 meters. Each column may have a varying size. In one embodiment, the ratio of column diameter in meters for all the distillation columns to tons of ethanol produced per hour is from 1:2 to 1:30, e.g., from 1:3 to 1:20 or from 1:4 to 1:10. This would allow the process to achieve production rates of 25 to 250 tons of ethanol per hour.

The distillate from the initial column comprises light organics, such as acetaldehyde, ethyl acetate, diethyl ether, and/or acetone. In addition, minor amounts of ethanol and water may be present in the distillate. Removing these light organic components from the crude ethanol product in the initial column provides an efficient means for removing acetaldehyde and ethyl acetate. In particular, acetaldehyde and/or ethyl acetate may be returned to the reactor, and converted to additional ethanol. In another embodiment, a purge may remove these light organics from the system.

The residue from the initial column may comprise ethyl acetate, either from the crude ethanol product or formed in situ after being withdrawn from the initial column. Although ethyl acetate is also partially withdrawn into the first distillate, a higher ethyl acetate concentration in the first residue leads to increased ethanol concentration in the first residue and decreased ethanol concentrations in the first distillate. Thus overall ethanol recovery may be increased. Ethyl acetate may be separated from ethanol in a separate column near the end of the purification process. In removing ethyl acetate, additional light organics may also be removed and thus improve the quality of the ethanol product by decreasing impurities. Preferably, water and/or acetic acid may be removed prior to the ethyl acetate/ethanol separation.

In one embodiment, after the ethyl acetate is separated from ethanol, the ethyl acetate is returned to the initial column and fed near the top of that column. This allows for any ethanol removed with the ethyl acetate to be recovered and further reduces the amount of ethanol being recycled to the reactor. Decreasing the amount of ethanol recycled to the reactor may reduce reactor capital and improve efficiency in recovering ethanol. Preferably, the ethyl acetate is removed in the distillate of the first column and returned to the reactor with the acetaldehyde.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{12}C$ ratio of the methanol, acetic acid and/or ethanol may be from one half to about 1 of the $^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180 and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof.

These other compounds may also be hydrogenated in the processes of the present invention. In some embodiments, the presence of carboxylic acids, such as propanoic acid or its aldehyde, may be beneficial in producing propanol. Water may also be present in the acetic acid feed. Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments, the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 99 wt. %, or from 80 to 97.5 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support and the support modifier is present in an amount from 0.1 to 50 wt. %, e.g., from 0.2 to 25 wt. %, from 1 to 20 wt. %, or from 3 to 15 wt. %, based on the total weight of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be crystalline or amorphous.

Catalysts on a modified support may include one or more metals from the group of platinum, palladium, cobalt, tin, or rhenium on a silica support modified by one or more modifiers from the group of calcium metasilicate, oxides of tungsten, molybdenum, and vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with high conversion, and the acetic acid concentration nay range from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Figure 2:
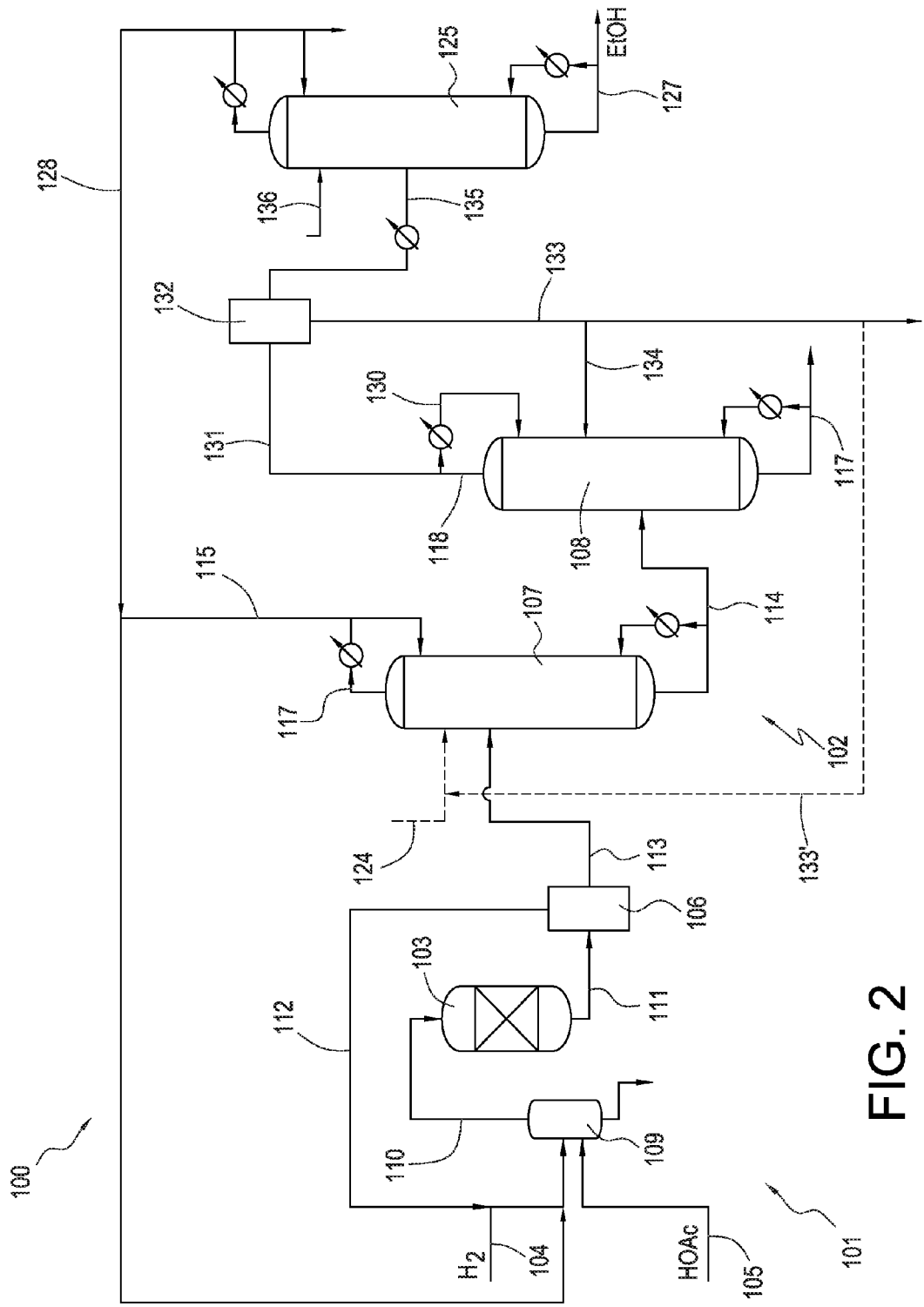
FIG. 2 is another schematic diagram of an ethanol production system with an intervening water separation step in accordance with one embodiment of the present invention.

Exemplary ethanol recovery systems in accordance with embodiments of the present invention are shown in FIGS. 1 and 2. Each hydrogenation system 100 provides a suitable hydrogenation reactor and a process for separating ethanol from the crude reaction mixture according to an embodiment of the invention. System 100 comprises reaction zone 101 and separation zone 102. Further modifications and additional components to reaction zone 101 and separation zone 102 are described below.

As shown in FIG. 1, the feed to reactor 103 comprises fresh acetic acid. Hydrogen and acetic acid are fed to vaporizer 109 via lines 104 and 105, respectively, to create a vapor feed stream in line 110 that is directed to reactor 103. In one embodiment, lines 104 and 105 may be combined and jointly fed to vaporizer 109. The temperature of the vapor feed stream in line 110 is preferably from 100° C. to 350° C., e.g., from 120° C. to 310° C. or from 150° C. to 300° C. Any feed that is not vaporized is removed from vaporizer 109, via blowdown 108. In addition, although line 110 is shown as being directed to the top of reactor 103, line 110 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 109, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 111.

The crude ethanol product may be condensed and fed to separator 106, which, in turn, forms a vapor stream 112 and a liquid stream 113. In some embodiments, separator 106 may comprise a flasher or a knockout pot. Separator 106 may operate at a temperature of from 20° C. to 350° C., e.g., from 30° C. to 325° C. or from 60° C. to 250° C. The pressure of separator 106 may be from 100 kPa to 3000 kPa, e.g., from 125 kPa to 2500 kPa or from 150 kPa to 2200 kPa. Optionally, the crude ethanol product in line 111 may pass through one or more membranes to separate hydrogen and/or other non-condensable gases.

Vapor stream 112 exiting separator 106 may comprise hydrogen and hydrocarbons, and may be purged and/or returned to reaction zone 101. As shown, vapor stream 112 is combined with the hydrogen feed 104 and co-fed to vaporizer 109. In some embodiments, the returned vapor stream 112 may be compressed before being combined with hydrogen feed 104.

Liquid stream 113 from separator 106 is withdrawn and directed as a feed composition to the side of first distillation column 107, also referred to as an "extractive column." Liquid stream 113 may be heated from ambient temperature to a temperature of up to 70° C., e.g., up to 50° C., or up to 40° C. The additional energy required to pre-heat liquid stream 113 above 70° C. does not achieve the desired energy efficiency in first column 107 with respect to reboiler duties. In another embodiment, liquid stream 113 is not separately preheated, but is withdrawn from separator 110, and cooled if need, at a temperature of less than 70° C., e.g., less than 50° C., or less than 40° C., and directly fed to first column 107.

In one embodiment, the contents of liquid stream 113 are substantially similar to the crude ethanol product obtained from the reactor, except that the composition has been depleted of hydrogen, carbon dioxide, methane or ethane, which have been removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

FEED COMPOSITION TO COLUMN 107
(Liquid Stream 113)

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present specification are preferably not present and if present may be present in trace amounts or in amounts greater than 0.0001 wt. %.

In one embodiment, the ethyl acetate concentration in the liquid stream 113 may affect the first column reboiler duty and size. Decreasing ethyl acetate concentrations may allow for reduced reboiler duty and size. In one embodiment, to reduce the ethyl acetate concentration (a) the catalyst in reactor may convert ethyl acetate in addition to acetic acid; (b) the catalyst may be less selective for ethyl acetate, and/or (c) the feed to reactor, including recycles, may contain less ethyl acetate.

In the embodiment shown in FIG. 1, liquid stream 113 is introduced in the upper part of first column 107, e.g., upper half or upper third. In addition to liquid stream 113, an optional extractive agent 124 and an optional ethyl acetate recycle stream 129 are also fed to first column. In first column 107, a weight majority of the ethanol, water, acetic acid, are removed from liquid stream 113 and are withdrawn as residue in line 114. In addition, ethyl acetate may also be present in the first residue in line 114. First column 107 also forms an overhead distillate, which is withdrawn in line 115, and which may be condensed and refluxed, for example, at a ratio of from 30:1 to 1:30, e.g., from 10:1 to 1:10 or from 1:5 to 5:1. The overhead distillate in stream 115 preferably comprises a weight majority of the acetaldehyde and ethyl acetate from liquid stream 113.

In one embodiment, first column 107 is a tray column having from 5 to 90 theoretical trays, e.g. from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 107 is operated under a controlled pressure of about 50 kPa, the temperature of the residue exiting in line 114 preferably is from 20° C. to 100° C., e.g., from 30° C. to 90° C. or from 40° C. to 80° C. The base of column 107 may be maintained at a relatively low temperature by withdrawing a residue stream comprising ethanol, ethyl acetate, water, and acetic acid, thereby providing an energy efficiency advantage. The temperature of the distillate exiting in line 115 from column 107 preferably at 50 kPa is from 10° C. to 80° C., e.g., from 20° C. to 70° C. or from 30° C. to 60° C. In some embodiments, the controlled pressure of first column 107 may range from 0.1 kPa to 102 kPa, e.g., from 0.1 kPa to 70 kPa, from 1 kPa to 60 kPa or from 1 kPa to 50 kPa.

In an exemplary embodiment, the energy requirements by first column 107 may be less than 3 MMBtu per ton of refined ethanol, e.g., less than 1.5 MMBtu per ton of refined ethanol or less than 1 MMBtu per ton of refined ethanol. As stated above, first column 107 may be an extractive distillation column that uses an extractive agent, such as water. The water may be supplied from an external source in line 124 or from within the separation process. When water is supplied from within the separation process, the water may be fed to the first column 107 from at least a portion of the second residue in line 117'. In some embodiments, water in line 124 and 117' may be combined prior to being fed to first column 107.

Exemplary components of the distillate and residue compositions for first column 107 are provided in Table 3 below. The distillate and residue compositions are shown for an extractive distillation column and a distillation column. The extractive agent in the extractive distillation column may be water. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN 107

|  | With Extractive Column Conc. (wt. %) | Without Extractive Column Conc. (wt. %) |
|---|---|---|
| Distillate |  |  |
| Ethyl Acetate | 10 to 85 | 10 to 65 |
| Acetaldehyde | 0.1 to 70 | 0.1 to 70 |
| Acetal | 0 to 5 | <0.1 |
| Acetone | 0 to 5 | <0.05 |
| Ethanol | 1 to 25 | 3 to 55 |
| Water | 0.1 to 20 | 0.1 to 20 |
| Acetic Acid | <2 | <2 |
| Residue |  |  |
| Acetic Acid | 0.01 to 50 | 0.01 to 50 |
| Water | 20 to 85 | 5 to 40 |
| Ethanol | 10 to 75 | 10 to 75 |
| Ethyl Acetate | 0 to 5 | 0.005 to 5 |

The ethyl acetate concentrations in Table 3 may represent the ethyl acetate separated from the crude ethanol and the ethyl acetate formed in situ in the residue. In an embodiment of the present invention, column 107 may be operated at a temperature, under controlled pressure, where most of the water, ethanol, and acetic acid are removed into the residue stream and only a small amount of ethanol and water is collected in the distillate stream due to the formation of binary and tertiary azeotropes. The weight ratio of water in the residue in line 114 to water in the distillate in line 115 may be greater than 1:1, e.g., greater than 2:1. There may be more water in the first residue in line 114 when water is optionally used as an extractive agent, e.g., up to 85 wt. %, or up to 80 wt. %. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

In some embodiments, the separation in first column 107 may be conducted without the addition of an azeotrope or extractive agent. However, it may be preferred to operate with the optional extractive agent.

In some embodiments, distillate in line 115 preferably is substantially free of acetic acid, e.g., comprising less than 1000 wppm, less than 500 wppm or less than 100 wppm acetic acid. The distillate may be purged from the system or recycled in whole or part to reactor 103. In some embodiments, when the distillate comprises ethyl acetate and acetaldehyde, the distillate may be further separated, e.g., in a distillation column (not shown), into an acetaldehyde stream and an ethyl acetate stream. The ethyl acetate stream may also be hydrolyzed or reduced with hydrogen, via hydrogenolysis, to produce ethanol. Either of these streams may be returned to reactor 103 or separated from system 100 as separate products. Some species, such as acetals, may decompose in first column 107 such that very low amounts, or even no detectable amounts, of acetals remain in the distillate or residue.

In addition, an equilibrium reaction between acetic acid/ethanol and ethyl acetate may occur in the crude ethanol product after existing reactor 103 or first column 115. Without being bound by theory, ethyl acetate may be formed in the reboiler of first column 115. Depending on the concentration of acetic acid in the crude ethanol product, this equilibrium may be driven toward formation of ethyl acetate. This reaction may be regulated through the residence time and/or temperature of the distillation column.

In one embodiment, due to the composition of first residue in line 114 the equilibrium may favor esterification to produce ethyl acetate. While the esterification, either in the liquid or vapor phase, may consume ethanol, the esterification may also reduce the amount of acetic acid that needs to be removed from the process. Ethyl acetate may be removed from first column 107 or formed in situ ethyl acetate via esterification between first column 107 and second column 108. The esterification may be further promoted by passing a portion of the first residue in line 114 through an esterification reactor (not shown). The esterification reactor may be either a liquid or vapor phase reactor and may comprise an acidic catalyst. A vapor phase reactor (not shown) may be used to convert some of the first residue into an intermediate vapor feed to be introduced into a second column 108. Acid-catalyzed esterification reactions may be used with some embodiments of the present invention. The catalyst should be thermally stable at reaction temperatures. Suitable catalysts may be solid acid catalysts comprising an ion exchange resin, zeolites, Lewis acid, metal oxides, inorganic salts and hydrates thereof, heteropoly acids and salts thereof. Silica gel, aluminum oxide, and aluminum phosphate are also suitable catalysts. Acid catalysts include, but are not limited to, sulfuric acid, and tosic acid. In addition, Lewis acids may also be used as esterification catalysts, such as scandium(III) or lanthanide (III) triflates, hafnium(IV) or zirconium(IV) salts, and diarylammonium arenesulfonates. The catalyst may also include sulfonated (sulphonic acid) ion-exchange resins (e.g., gel-type and macroporous sulfonated styrene-divinyl benzene IERs), sulfonated polysiloxane resins, sulfonated perfluorinated (e.g., sulfonated poly-perfluoroethylene), or sulfonated zirconia.

To recover ethanol, first residue in line 114 may be further separated depending on the concentration of acetic acid and/or ethyl acetate. In most embodiments of the present invention, residue in line 114 is further separated in a second column 108. In FIG. 1, the second column is referred to as an "acid column." Second column 108 yields a second residue in line 117 comprising acetic and water, and a second distillate in line 118 comprising ethanol and ethyl acetate. In one embodiment, a weight majority of the water and/or acetic acid fed to second column 108 is removed in the second residue 117, e.g., at least 60% of the water and/or acetic acid is removed in the second residue in line 117 or more preferably at least 80% of the water and/or acetic acid. An acid column may be desirable, for example, when the acetic acid concentration in the first residue is greater 50 wppm, e.g., greater than 0.1 wt. %, greater than 1 wt. %, e.g., greater than 5 wt. %.

In FIGS. 1 and 2, the first residue in line 114 is introduced to second column 108, e.g., acid column, preferably in the top part of column 108, e.g., top half or top third. Feeding first residue in line 114 in a lower portion of second column 108 may unnecessarily increase the energy requirement of second column 108. Acid column 108 may be a tray column or packed column. In FIGS. 1 and 2, second column 108 may be a tray column having from 10 to 110 theoretical trays, e.g., from 15 to 95 theoretical trays or from 20 to 75 theoretical trays. Additional trays may be used if necessary to further reduce the ethanol concentration in the residue. In one embodiment, the reboiler duty and column size may be reduced by increasing the number of trays.

Although the temperature and pressure of second column 108 may vary, when at 170 kPa, the temperature of the second residue in line 117 preferably is from 95° C. to 160° C., e.g., from 100° C. to 150° C. or from 110° C. to 145° C. In one embodiment, when first residue in line 118 is preheated to a temperature that is within 20° C. of the temperature of second residue in line 117, e.g., within 15° C. or within 10° C. The temperature of the second distillate exiting in line 118 from second column 108 preferably is from 50° C. to 120° C., e.g., from 75° C. to 118° C. or from 80° C. to 115° C. The temperature gradient may be sharper in the base of second column 130. In one embodiment, second column 108 operates above atmospheric pressure, e.g., above 170 kPa or above 375 kPa. Second column 108 may be constructed of a material such as 316L SS, Allot 2205 or Hastelloy C, depending on the operating pressure. The reboiler duty and column size for second column remain relatively constant until the ethanol concentration in the second distillate in line 118 is greater than 90 wt. %.

The pressure of second column 108 may range from 70 kPa to 510 kPa, e.g., from 70 kPa to 475 kPa, from 70 kPa to 350 kPa or from 70 kPa to 200 kPa.

Exemplary components for the distillate and residue compositions for second column 108 are provided in Table 4 below. It should be understood that the distillate and residue may also contain other components, not listed in Table 4. For example, in optional embodiments, when ethyl acetate is in the feed to reactor 103, second residue in line 131 exemplified in Table 4 may also comprise high boiling point components.

TABLE 4

| ACID COLUMN 108 | | | |
|---|---|---|---|
| | Conc. (wt. %) | Conc. (wt. %) | Conc. (wt. %) |
| Second Distillate | | | |
| Ethanol | 80 to 96 | 85 to 92 | 87 to 90 |
| Ethyl Acetate | <30 | 0.001 to 15 | 0.005 to 4 |
| Acetaldehyde | <20 | 0.001 to 15 | 0.005 to 4 |
| Water | <20 | 0.001 to 10 | 0.01 to 8 |
| Acetal | <2 | 0.001 to 1 | 0.005 to 0.5 |
| Second Residue | | | |
| Acetic Acid | 0.1 to 55 | 0.2 to 40 | 0.5 to 35 |
| Water | 45 to 99.9 | 55 to 99.8 | 65 to 99.5 |

TABLE 4-continued

| ACID COLUMN 108 | | | |
|---|---|---|---|
| | Conc. (wt. %) | Conc. (wt. %) | Conc. (wt. %) |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in the second distillate in line 118 to ethanol in the second residue in line 117 preferably is at least 35:1. In one embodiment, the weight ratio of water in the second residue 117 to water in the second distillate 118 is greater than 2:1, e.g., greater than 4:1 or greater than 6:1. In addition, the weight ratio of acetic acid in the second residue 117 to acetic acid in the second distillate 118 preferably is greater than 10:1, e.g., greater than 15:1 or greater than 20:1. Preferably, the second distillate in line 118 is substantially free of acetic acid and may only contain, if any, trace amounts of acetic acid. A reduced concentration of acetic acid in line 118 advantageously provides an ethanol product that also has no amount or a trace amount of acetic acid.

In some optional embodiments, when ethyl acetate is used alone as a feed, the second residue exemplified in Table 4 may comprise high boiling point components. Preferably, these higher boiling point components comprise alcohols having more than two carbon atoms.

In one embodiment, ethyl acetate fed to second column 108 may concentrate in the second distillate in line 118. Thus, preferably no ethyl acetate is withdrawn in the second residue in line 117. Advantageously this allows most of the ethyl acetate to be subsequently recovered without having to further process the second residue in line 117.

As shown in FIG. 1, a third column 125, referred to as a "light ends" column, is used for removing ethyl acetate from the second distillate in line 118 and producing an ethanol product in line 127. Light ends column 125 may be a tray column or packed column. In FIG. 1, third column 125 may be a tray column having from 5 to 90 theoretical trays, e.g. from 10 to 60 theoretical trays or from 15 to 50 theoretical trays.

Second distillate in line 118 may be fed to third column 125 at a temperature of up to 70° C., e.g., up to 50° C., or up to 40° C. In some embodiments it is not necessary to further preheat second distillate in line 118.

Ethyl acetate may be concentrated in the third distillate in line 128. Due to the relatively lower amounts of ethyl acetate fed to third column 125, third distillate in line 128 also comprises substantial amounts of ethanol. To recover the ethanol, third distillate in line 128 may be fed to first column as the ethyl acetate recycle stream 107. Because this increased the demands on the first and second columns, it is preferred that the concentration of ethanol in third distillate in line 128 be from 70 to 90 wt. %, e.g., from 72 to 88 wt. %, or from 75 to 85 wt. %.

In other embodiments, a portion of third distillate may be purged from the system in line 128 as additional products, such as an ethyl acetate solvent.

In some embodiments to recover the ethanol without sending third distillate in line 128 back to first column 107, the ethanol may be recovered using an extractive column (not shown).

The third residue in line 127 from third column 125 may comprise ethanol and optionally any remaining water. The third residue may be further processed to recover ethanol with a desired amount of water, for example, using a further distillation column, adsorption unit, membrane or combination thereof, may be used to further remove water from third residue in line 127 as necessary.

Third column 125 is a tray column, preferably a packed tray column as described above, and preferably operates a controlled pressure from 0.1 kPa to 102 kPa, e.g., from 0.1 kPa to 70 kPa, from 1 kPa to 60 kPa or from 1 kPa to 50 kPa. In some embodiments, both first column 107 and third column 125 operate at the same controlled pressure. The temperature of the third residue exiting from third column 125 may vary, and when at 50 kPa, preferably is from 70° C. to 115° C., e.g., from 70° C. to 100° C. or from 75° C. to 95° C. The temperature of the third distillate exiting from third column 125 may vary, and when at 50 kPa, preferably is from 60° C. to 110° C., e.g., from 80° C. to 110° C. or from 85° C. to 105° C., when the column is operated at 50 kPa. In an exemplary embodiment, the energy requirements by third column 125 in the process according to the present invention may be less than 3 MMBtu per ton of refined ethanol, e.g., less than 2 MMBtu per ton of refined ethanol or less than 1.5 MMBtu per ton of refined ethanol.

The remaining water from the second distillate in line 118 may be removed in further embodiments of the present invention. Depending on the water concentration, the ethanol product may be derived from the second distillate in line 118. Some applications, such as industrial ethanol applications, may tolerate water in the ethanol product, while other applications, such as fuel applications, may require an anhydrous ethanol. The amount of water in the distillate of line 118 may be closer to the azeotropic amount of water, e.g., at least 4 wt. %, preferably less than 20 wt. %, e.g., less than 12 wt. % or less than 7.5 wt. %. Water may be removed from the second distillate in line 118 using several different separation techniques. Particularly preferred techniques include the use of distillation column, membranes, adsorption units and combinations thereof.

In one embodiment, water may be removed prior to light ends column 125. In one embodiment, the second distillate in line 118 may comprise less than 15 wt. % water, e.g., less than 10 wt. % water or less than 8 wt. % water. As shown in FIG. 2, the second distillate in line 118 may be fed in line 131 to water separator 132 to water separator 132, which may be an adsorption unit, membrane, molecular sieves, extractive distillation column, or a combination thereof. In one embodiment, at least 50% of overhead vapor is fed to water separator 132, e.g., at least 75% or at least 90%. Optionally, some of the distillate in line 118, preferably a condensed portion in line 130, may be fed directly to third distillation column 125, as shown in line 136.

In a preferred embodiment, water separator 132 is a pressure swing adsorption (PSA) unit. For purposes of clarity the details of the PSA unit are not shown in the figures. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 132 may remove at least 95% of the water from the second distillate in line 131, and more preferably from 95% to 99.99% of the water from the second distillate, in a water stream 133. All or a portion of water stream 133 may be returned to column 108 in line 134, which may increase the reboiler duty and/or size of second column 108. Optionally, at least a portion of water stream 133 may be fed to first column 107 in line 133', alone or in combination with an optional external water source in line 124. Additionally or alternatively, all or a portion of water stream 133 may be purged. The remaining portion of second distillate 131 exits the water separator 132 as ethanol mixture stream 135. In one embodiment, ethanol mixture stream 135 comprises more than 92 wt. % ethanol, e.g., more than 95 wt. % or more than 99 wt. %. In one embodiment a portion of water stream 133 may be fed to first column 107 as the extractive agent.

A portion of second distillate 118 may be condensed and refluxed to second column 108, as shown, for example, at a ratio from 12:1 to 1:12, e.g., from 10:1 to 1:10 or from 8:1 to 1:8. The second distillate in line 118 optionally may be mixed with ethanol mixture stream 135 and co-fed to light ends column 125. This may be necessary if additional water is needed to improve separation in light ends column 125. It is understood that reflux ratios may vary with the number of stages, feed locations, column efficiency and/or feed composition. Operating with a reflux ratio of greater than 3:1 may be less preferred because more energy may be required to operate second column 130.

Exemplary components for ethanol mixture stream and residue compositions for third column 140 are provided in Table 5 below. It should be understood that the distillate and residue may also contain other components, not listed in Table 5.

TABLE 5

| LIGHT ENDS COLUMN | | | |
|---|---|---|---|
| | Conc. (wt. %) | Conc. (wt. %) | Conc. (wt. %) |
| Third Distillate | | | |
| Ethanol | 70 to 99 | 72 to 95 | 75 to 90 |
| Ethyl Acetate | 0.5 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Water | <8 | 0.001 to 3 | 0.01 to 1 |
| Ethyl Acetate | <1.5 | 0.0001 to 1 | 0.001 to 0.5 |
| Acetic Acid | <0.5 | <0.01 | 0.0001 to 0.01 |

In one embodiment, the third residue in line 127 may comprise from 75 to 96 wt. % ethanol and less than 12 wt. % water, more preferably less than 3 wt. % water. Depending on the desired ethanol application and on the concentration of organics in the third distillate, the resulting third residue in line 127 may be withdrawn from the system as the finished ethanol product. For some ethanol applications, it may be desirable to remove residual water from the third residue in line 127. Residual water removal may be accomplished, for example, using one or more adsorption units, membranes, molecular sieves, extractive distillation units, or a combination thereof. Suitable adsorption units include pressure swing adsorption systems and thermal swing adsorption units.

Depending on the amount of water and acetic acid contained in the second residue of second column 108, line 117 may be treated in one or more of the following processes. A suitable weak acid recovery system is described in U.S. Pub. No. 2012/0010446, the entire contents and disclosure of which is hereby incorporated by reference. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by distillation columns or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where second residue in line 117 comprises less than 50 wt. % acetic acid, possible options include one or more of: (i) returning a portion of the residue to reactor 103, (ii) neutralizing the acetic acid, or (iii) disposing of the residue in a waste water treatment facility. It also may be possible to separate a residue using weak acid recovery distillation columns to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 117 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the second residue in line 117 comprises very minor amounts of acetic acid, e.g., less than 5 wt. %, the residue may be disposed of to a waste water treatment facility after neutralization and/or dilution. The organic content, e.g., acetic acid content, of the residue beneficially may be suitable to feed microorganisms used in a waste water treatment facility.

The ethanol product produced by the process of the present invention may be an industrial grade ethanol or fuel grade ethanol. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
| --- | --- | --- | --- |
| Ethanol | 85 to 99.9 | 90 to 99.5 | 92 to 99.5 |
| Water | <8 | 0.1 to 3 | 0.1 to 1 |
| Acetic Acid | <1 | <0.1 | <0.01 |
| Ethyl Acetate | <2 | <0.5 | <0.05 |
| Acetal | <0.5 | <0.1 | <0.05 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene.

In order that the invention disclosed herein may be more efficiently understood, an examples is provided below. It should be understood that this example is for illustrative purposes only and is not to be construed as limiting the invention in any manner.

EXAMPLES

Example 1

A separation process according to this invention was used. A crude ethanol product obtained by converting 90% of acetic acid was fed to a separation system comprising three columns. After hydrogen and non-condensable gases were removed, the liquid feed to the columns contained 60.2 wt. % ethanol, 19.3 wt. % water, 12.7 wt. % ethyl acetate, 6.4 wt. % acetic acid, and less than 1 wt. % of acetaldehyde, diethyl acetal, and diethyl ether. The first and third columns were operated at 46 kPa and the second column was operated at 170 kPa.

Example 2

In a comparative process, the first, second and third columns were operated at 170 kPa. The energy requirements for Example 1 and 2 are disclosed in Table 6.

TABLE 6

ENERGY REQUIREMENTS AS MMBTU/TONNE PRODUCT ETHANOL

| Example | First Column | Second Column | Third Column | Total |
| --- | --- | --- | --- | --- |
| Example 1 | 0.6 | 3.2 | 0.5 | 4.5 |
| Example 2 | 0.9 | 3.2 | 1.1 | 5.2 |

In addition to the lower energy requirements, Example 1 also recovered 92% of the ethanol from the crude ethanol product, while Example 2 recovered 88%. The ethanol product contained at least 92 wt. % ethanol, and less than 0.01 wt. % of organic impurities, with the balance being water.

Example 3

In a comparative process, the first column was operated under atmospheric pressure and compared with the first column operated under a reduced pressure of approximately 33 kPa. The energy requirement, ethanol yield, and relative column cost are disclosed in Table 7.

TABLE 7

COMPARISON OF FIRST COLUMN

|  | Atmospheric Pressure | Reduced Pressure |
| --- | --- | --- |
| Energy Requirements [MMBtu/ton Ethanol] | 1.66 | 0.68 |
| Ethanol Recovered in Residue | 87.1% | 90.1% |

As shown in Table 7, when the first column was operated under reduced pressure, the energy requirements for the column reduced from 1.66 to 0.68. At the same time, the amount of ethanol recovered increased from 87.1% to 90.1%. Furthermore, the cost to operate the column under reduced pressure reduced the operation cost by 13%.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
hydrogenating acetic acid and/or an ester thereof in a reactor in the presence of a catalyst to form a crude ethanol product;
separating a portion of the crude ethanol product in a first distillation column to yield a first distillate comprising acetaldehyde and a first residue comprising ethanol, acetic acid, ethyl acetate and water;
separating a portion of the first residue in a second distillation column to yield a second residue comprising acetic acid and water and a second distillate comprising ethanol and ethyl acetate; and
separating at least a portion of the second distillate in a third distillation column to yield a third distillate comprising ethyl acetate and a third residue comprising ethanol,
wherein the first distillation column and the third distillation column are operated at a lower pressure than the second distillation column.

2. The process of claim 1, wherein the first and/or third distillation column is an extractive distillation column.

3. The process of claim 2, wherein the extractive distillation column comprises an extractive agent comprising water.

4. The process of claim 1, wherein the first and third distillation column are operated at the same pressure.

5. The process of claim 1, wherein the first and/or third distillation column is operated at a pressure from 0.1 kPa to 102 kPa.

6. The process of claim 1, wherein the first and/or third distillation column is operated at a pressure from 1 kPa to 50 kPa.

7. The process of claim 1, wherein the second distillation column is operated at a pressure of at least 70 kPa.

8. The process of claim 1, wherein the second distillation column is operated at a pressure from 70 kPa to 510 kPa.

9. The process of claim 1, wherein at least 90% of the ethanol in the crude ethanol product is withdrawn into the first residue stream.

10. The process of claim 1, wherein the first residue comprises more than 10 wppm ethyl acetate.

11. The process of claim 1, further comprising returning at least a portion of the third distillate to the first distillation column.

12. The process of claim 1, further comprising returning at least a portion of the first distillate to the reactor.

13. The process of claim 1, wherein the first distillate comprises ethyl acetate.

14. The process of claim 1, further comprising recovering acetic acid from the second residue and returning at least a portion of the recovered acetic acid to the reactor.

15. The process of claim 1, further comprising directing at least a portion of the second residue to a waste water treatment facility to feed microorganisms used in the waste water treatment facility.

16. The process of claim 1, wherein the second residue comprises 0.1 to 10 wt. % acetic acid, the process further comprising the step of neutralizing and/or diluting the acetic acid from the second residue.

17. The process of claim 1, wherein the second distillate is substantially free of acetic acid.

18. The process of claim 1, further comprising removing water from at least a portion of the second distillate using an adsorption unit, membrane, extractive column distillation, molecular sieve, or a combination thereof to yield an ethanol product having a lower water content than the at least a portion of the second distillate.

19. The process of claim 18, wherein the third residue comprises less than 3 wt. % water.

20. The process of claim 1, wherein at least some of the acetic acid in the first residue is reacted with ethanol to form an ester enriched stream in the first residue or in the second column.

21. The process of claim 1, wherein the first residue is fed to an esterification reactor comprising an acidic catalyst.

22. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

23. A process for producing ethanol, comprising:
providing a crude ethanol product comprising ethanol, acetic acid, ethyl acetate, acetaldehyde, and water;
separating a portion of the crude ethanol product in a first distillation column to yield a first distillate comprising acetaldehyde and ethyl acetate and a first residue comprising ethanol, ethyl acetate, acetic acid and water;
separating a portion of the first residue in a second distillation column to yield a second residue comprising acetic acid and water and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated at a lower pressure than the second distillation column.

24. A process for producing ethanol comprising:

providing a crude ethanol product comprising ethanol, ethyl acetate, acetaldehyde, and water;

separating at least a portion of the crude ethanol product in a first distillation column to form a first distillate comprising acetaldehyde and ethyl acetate and a first residue comprising ethanol and water;

separating at least a portion of the first residue to form an organic stream comprising ethanol and an aqueous stream comprising water; and separating the organic stream in a second distillation column to form a second distillate comprising ethanol and a second residue comprising water, wherein the first distillation column is operated at a lower pressure than the second distillation column.

25. The process of claim 24, further comprising recycling the aqueous stream to the first distillation column.

26. A process for producing ethanol comprising:

hydrogenating acetic acid and/or an ester thereof in a reactor in the presence of a catalyst to form a crude ethanol product;

separating a portion of the crude ethanol product in a first distillation column to yield a first distillate comprising acetaldehyde and ethyl acetate and a first residue comprising ethanol, ethyl acetate, acetic acid and water;

separating a portion of the first residue in a second distillation column to yield a second residue comprising acetic acid and a second distillate comprising ethanol, ethyl acetate and water;

removing water from at least a portion of the second distillate to yield an ethanol product having a lower water content than the at least a portion of the second distillate; and separating at least a portion of the ethanol product in a third distillation column to yield a third distillate comprising ethyl acetate and a third residue comprising ethanol and less than 3 wt. % water, wherein the first distillation column and the third distillation column are operated at a lower pressure than the second distillation column.

27. The process of claim 26, wherein an adsorption unit, membrane, extractive column distillation, molecular sieves, or a combination thereof is used for removing water.

28. The process of claim 26, wherein the water removed from at least a portion of the second distillate is recycled to the first distillation column.

29. A process for producing ethanol comprising:

hydrogenating acetic acid and/or an ester thereof in a reactor in the presence of a catalyst to form a crude ethanol product;

separating a portion of the crude ethanol product in a first distillation column to yield a first distillate comprising acetaldehyde and a first residue comprising ethanol, acetic acid and/or ethyl acetate;

separating a portion of the first residue in a second distillation column to yield a second residue comprising high boiling point components and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated at a lower pressure than the second distillation column.

30. The process of claim 29, wherein the high boiling point components are selected from the group consisting of acetic acid, water, alcohols having more than 2 carbon atoms, and mixtures thereof.

31. A process for producing ethanol comprising:

hydrogenating acetic acid and/or an ester thereof in a reactor in the presence of a catalyst to form a crude ethanol product;

separating a portion of the crude ethanol product in a first distillation column to yield a first distillate comprising acetaldehyde and a first residue comprising ethanol, acetic acid and/or ethyl acetate;

separating a portion of the first residue in a second distillation column to yield a second residue comprising high boiling point components and a second distillate comprising ethanol and ethyl acetate; and separating at least a portion of the second distillate in a third distillation column to yield a third distillate comprising ethyl acetate and a third residue comprising ethanol, wherein the first distillation column and the third distillation column are operated below atmospheric pressure.

* * * * *